United States Patent [19]

Evans et al.

[11] 4,107,176
[45] Aug. 15, 1978

[54] MONO-N-TOSYLSULFIMIDES, THEIR PREPARATION AND THEIR REACTION PRODUCTS

[75] Inventors: David H. Evans; Richard B. Greenwald, both of Cambridge, Mass.

[73] Assignee: Polaroid Corporation, Cambridge, Mass.

[21] Appl. No.: 764,862

[22] Filed: Feb. 2, 1977

Related U.S. Application Data

[63] Continuation-in-part of Ser. No. 679,487, Apr. 23, 1976, abandoned, which is a continuation-in-part of Ser. No. 591,463, Jun. 30, 1975, abandoned.

[51] Int. Cl.$^2$ .................. C07D 339/08; G03C 5/26
[52] U.S. Cl. ........................... 260/327 M; 96/50 R
[58] Field of Search ........ 260/327 M, 556 AR, 551 S, 260/556 A

[56] References Cited

U.S. PATENT DOCUMENTS

| | | | |
|---|---|---|---|
| 3,107,229 | 10/1963 | Malz et al. ........................... | 260/45.8 |
| 3,542,865 | 11/1970 | Bayer ................................... | 260/556 |
| 3,794,669 | 2/1974 | Wynberg et al. .................. | 260/397.2 |

OTHER PUBLICATIONS

Emerson, et al., Tetrahedron Letters, No. 37, pp. 3445–3448 (1971).
Breslow, et al., Chem. of Het. Compounds, vol. 21, Part 2, pp. 998–1007.
Howard, et al., J.A.C.S. 82: 158–164 (1–1960).
Mann et al., J. Chem. Soc., 1922: T1052–1055.
Nicolet, et al., Science 53: 217 (1921).

Primary Examiner—Cecilia M. Jaisle
Attorney, Agent, or Firm—Sybil A. Campbell

[57] ABSTRACT

This application is directed to cycloalkanes containing the moiety —$SO_2$—$CH_2$—X— wherein X represents

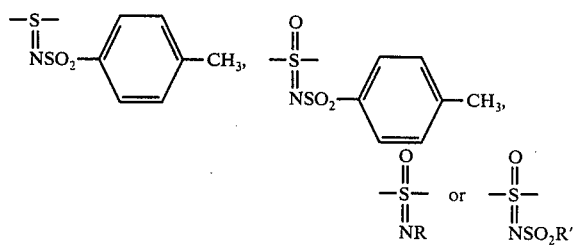

wherein R is hydrogen or alkyl and R' is alkyl and to the preparation of these compounds which find utility as silver halide complexing agents. This application is also concerned with cycloalkanes containing the moiety

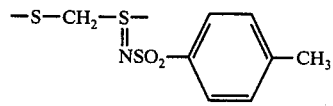

useful as intermediates in the preparation of the aforementioned compounds. Also included within the confines of this disclosure are the 2-thioether-substituted derivatives of certain of the above-identified cycloalkanes and with the synthesis of all of these compounds.

71 Claims, No Drawings

MONO-N-TOSYLSULFIMIDES, THEIR PREPARATION AND THEIR REACTION PRODUCTS

CROSS-REFERENCE TO RELATED APPLICATIONS

This application is in part a continuation of copending application Ser. No. 679,487 filed Apr. 23, 1976, now abandoned which is a continuation-in-part of copending application Ser. No. 591,463 filed June 30, 1975, now abandoned.

BACKGROUND OF THE INVENTION

1. Field of the Invention

This invention relates to novel chemical compounds useful as silver halide complexing agents, to novel intermediates useful in the synthesis of said compounds and to processes for the preparation thereof.

2. Description of the Prior Art

The protection of carbonyl groups during synthesis is well-known, and the importance of ethylene thioketal and hemithioketal (or -acetal) protecting groups in steroid chemistry has been discussed by L. F. Fieser and M. Fieser, Steroids, Reinhold, 1959, pp. 307–310 and C. Djerassi, Steroid Reactions, Holden-Day, 1963, pp. 21–34.

Recently, D. W. Emerson and H. Wynberg. Tetrahedron Letters, 1971, p. 3445 and W. F. J. Huurdman, H. Wynberg and D. W. Emerson, ibid., 1971, p. 3449 reported the facile cleavage of 2-substituted 1,3-dithianes and related compounds with N-chloro-p-toluenesulfonamide sodium salt (Chloroamine-T) under mild conditions, thus making these systems useful as carbonyl protecting functions. It has been postulated by D. W. Emerson and H. Wynberg that the mono-N-tosylsulfimides of various 2-alkyl substituted dithio and oxathio heterocycles open to produce a stabilized carbonium ion which subsequently undergoes fragmentation leading to a carbonyl compound.

In one aspect, the present invention is concerned with this reaction as applied to 1,3-dithianes and related compounds that are unsubstituted in the 2-position, and in another aspect is concerned with the oxidation and oxidation products of the mono-N-tosylsulfimides produced by the aforementioned reaction of N-chloro-p-toluenesulfonamide sodium salt with 2-unsubstituted dithiocycloalkanes. In addition, this invention is concerned with imino cleavage products of the oxidized compounds and derivatives thereof and with certain thioether-substituted compounds derived from these compounds.

SUMMARY OF THE INVENTION

It is one object of the present invention to provide novel cycloalkanes and 2-thioether-substituted derivatives of these compounds which cycloalkanes contain (a) an intralinear sulfonyl group and (b) an intralinear group selected from N-tosylsulfimido, N-tosylsulfoximido, N-alkylsulfonylsulfoximido, sulfoximino and N-alkylsulfoximino wherein said groups (a) and (b) are separated by a single methylene group.

It is another object of the present invention to provide a method of preparing said cycloalkanes and said thioether-substituted derivatives thereof.

It is yet another object of the present invention to provide novel intermediates useful in the preparation of the above-denoted cycloalkanes, said intermediates comprising cycloalkanes containing (a) an intralinear sulfur atom and (b) an intralinear N-tosylsulfimido group wherein said groups (a) and (b) are separated by a single methylene or methine group.

It is a further object of the present invention to provide a method of synthesizing said intermediates.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

According to the present invention, it has been found quite unexpectedly that the mono-N-tosylsulfimides produced by the reaction of N-chloro-p-toluenesulfonamide sodium salt with 1,3-dithiacycloalkanes unsubstituted in the 2-position, i.e., possessing two hydrogen atoms on the carbon atom in the 2-position, do not cleave to formaldehyde. As illustrated in the following reaction scheme, reaction of 1,3-dithiane (1) with one or two equivalents of Chloramine-T in 95% methanol-water or in other solvents particularly pyridine at ambient temperatures led to the isolation of the mono-N-tosylsulfimide (2) as a stable crystalline solid in 60% by weight yield. No indications were found for the formation of the bis-N-tosylsulfimide, even when large excesses of Chloramine-T were employed and the reaction mixture was subject to prolonged reflux. Apparently there is insufficient stabilization of the intermediate carbonium ion which would result from ring fission of (2) to promote the breakdown of the 2-unsubstituted 1,3-dithiane system. This supposition was supported when acetone was isolated (as the 2,4-dinitrophenylhydrazone) from the complex reaction mixture produced by the treatment of 2,2-dimethyl-1,3-dithiane with Chloramine-T under the same conditions employed for the preparation of (2).

It also has been found, as illustrated in the following reaction sequence, that the unfunctionalized sulfur of these mono-N-tosylsulfimides may be selectively oxidized to give the corresponding sulfonyl/N-tosylsulfimide which compounds may be further oxidized to the corresponding sulfonyl/N-tosylsulfoximides. Selective oxidation of the unfunctionalized sulfur of (2) was performed at room temperature using three equivalents of 40% peracetic acid to give (3) in 60% by weight crude yield. Attempts to further oxidize (3) with peracid at room temperature were unsuccessful, while at elevated temperatures only the disulfone (5) was isolated. Complete oxidation of (3) to (4) could be accomplished in 60% by weight yield in an acetic acid-acetic anhydride solvent system using about 2 molar equivalents of potassium permanganate. Alternatively, the mono-N-tosylsulfimide may be oxidized directly to the corresponding sulfonyl/N-tosylsulfoximide using potassium permanganate. For example, (4) was obtained by potassium permanganate oxidation of (2) using between about 6 and 7 molar equivalents of oxidant.

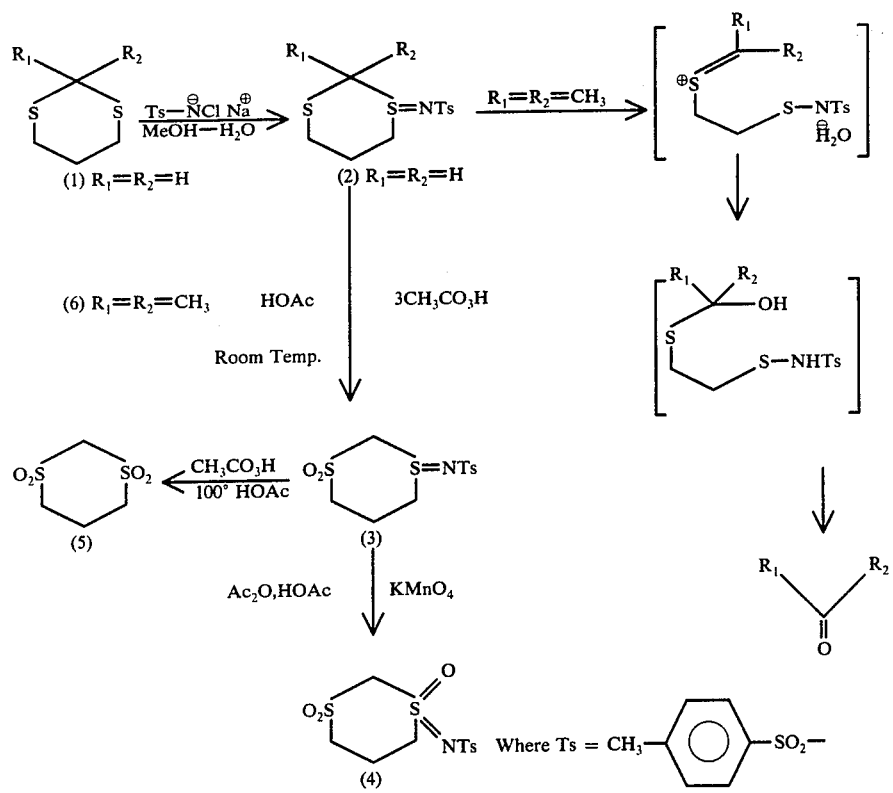

Other 2-unsubstituted 1,3-dithianes were found to react analogously to (1) as illustrated below wherein (7) gave in about 50% by weight yield a single mono-N-tosylsulfimide (8), the structure of which was assigned on the basis of its $^{13}$C/nmr spectrum.

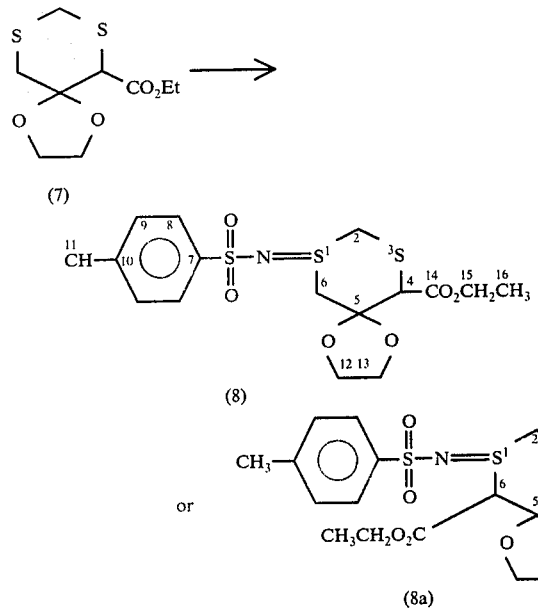

The data employed in assigning the structure (8) appears in Table I below. It is evident from reference to this Table that there are similar deviations in the calculated and observed $^{13}$C nmr chemical shift values for carbon atoms $C_2$, $C_5$, and $C_6$ of the two possible isomers (8) and (8a). For structure (8a) steric interaction at $C_4$ should be substantial, but the deviations show that the steric interaction decreases in the order $C_5 > C_2 > C_6 >> C_4$. Thus, the $^{13}$C nmr data are consistent only with structure (8) where this order of steric interaction would be anticipated.

TABLE I

Comparison of $13_{C_{nmr}}$ Shifts (PPM) Observed with those Calculated for Ring Carbon Atoms

| C Atom-n | Calculated Shifts* | | Observed Shifts | Deviation | |
|---|---|---|---|---|---|
| Isomer | (8) | (8a) | | (8) | (8a) |
| 2 | 146.5 | 146.5 | 143.3 | +3.2 | +3.2 |
| 4 | 150.9 | 150.6 | 150.4 | +0.5 | +0.2 |
| 5 | 94.2 | 94.2 | 88.4 | +5.8 | +5.8 |
| 6 | 150.6 | 150.9 | 152.2 | −1.6 | −1.3 |

*Calc. by the semi-empirical equation:

$$\delta \frac{(8)}{C_n} = \delta \frac{(1)}{C_n} + [\delta \frac{(1)}{C_n} \cdot \delta \frac{(3)}{C_n}] + [\delta \frac{(1)}{C_n} - \delta \frac{(7)}{C_n}]$$

The $^{13}$Cnmr chemical shifts for compounds 1, 2, 7 and 8 appear in Table II below.

Table II

| | Chemical Shifts* Compounds | | | |
|---|---|---|---|---|
| C Atom | (1) | (2) | (7) | (8) |
| 2 | 162.8 | 147.2 | 162.2 | 143.3 |
| 4 | 164.8 | 167.2 | 148.5 | 150.4 |
| 5 | 167.4 | 167.5 | 94.2 | 88.4 |
| 6 | 164.8 | 147.3 | 168.1 | 152.5 |
| 7 | | 51.7 | | 52.2 |
| 8 | | 68.2 | | 68.1 |
| 9 | | 64.5 | | 64.4 |
| 10 | | 52.7 | | 52.3 |
| 11 | | 173.0 | | 173.0 |
| 12 | | | 128.8 | 127.9 |
| 13 | | | 128.8 | 128.1 |
| 14 | | | 24.5 | 25.4 |
| 15 | | | 133.0 | 132.2 |
| 16 | | | 180.0 | 180.0 |

*$13_{C_{nmr}}$ chemical shifts are reported in parts per million (ppm) from external $13_{CS_2}$ in DMSO-$d_6$, and were recorded on a Varian CFT-20 spectrophotometer.

The sulfonyl/N-tosylsulfoximides as exemplified by (4) may be converted to the corresponding sulfonyl/sulfoximine by heating with strong mineral acid or by treating with metallic sodium in liquid ammonia. The sulfonyl/sulfoximines may be converted to the corresponding sulfonyl/N-alkylsulfoximines by reaction with an alkylfluorosulfonate and may be converted to the corresponding sulfonyl/N-alkylsulfonylsulfoximides by reaction with an alkanesulfonylchloride. The 2-unsubstituted compounds thus prepared may be converted to the corresponding 2-thioethers by reaction with the appropriate S-containing alkylating agent.

The novel compounds of the present invention are those represented by formula I below:

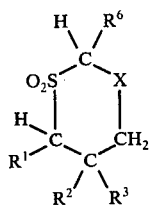
(I)

wherein $R^1$ is selected from hydrogen, alkyl and carboalkoxy; $R^2$ and $R^3$ when taken individually are selected from hydrogen and alkyl and $R^2$ and $R^3$ when taken together are spiro[1,3-dioxolane-2]; $R^6$ is selected from hydrogen and —$(CH_2)_nSR^o$ wherein $n$ is 0 or a positive integer other than 1 and $R^o$ is an inert hydrocarbon radical; and X is selected from

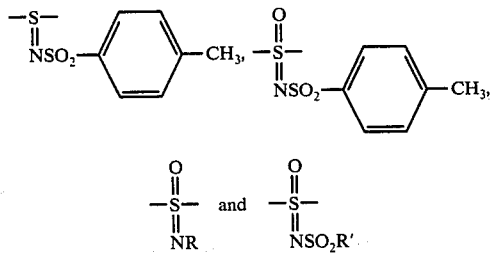

wherein R is selected from hydrogen and alkyl and R' is alkyl. In a preferred embodiment, the alkyl groups are lower alkyl containing 1 to 4 carbon atoms, for example, methyl, ethyl, propyl, isopropyl, s-butyl and n-butyl and the carboalkoxy group is —$CO_2R^4$ wherein $R^4$ is lower alkyl containing 1 to 4 carbon atoms.

In preparing the 2-unsubstituted compounds according to the present invention, a 1,3-dithiane having the formula

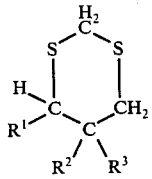
(II)

wherein $R^1$, $R^2$ and $R^3$ have the same meaning given in formula I above is reacted with N-chloro-p-toluenesulfonamide sodium salt in aqueous alkanol solution at a temperature between about 20° and 30° C. to yield the corresponding mono-N-tosylsulfimide having the formula

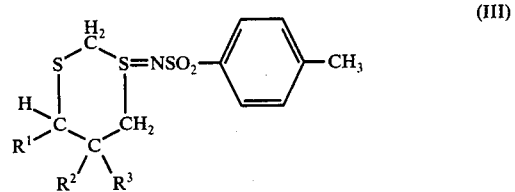
(III)

wherein $R^1$, $R^2$ and $R^3$ have the same meaning given in formula I above. These compounds represent the novel intermediates of the present invention. In this reaction, the solution generally is an aqueous solution of a lower alkanol having 1 to 4 carbon atoms, e.g., methanol or ethanol and contains between about 75 and 95% by weight of the alkanol. At least one molar equivalent and usually between about one and two molar equivalents of the N-chloro toluenesulfonamide sodium salt are reacted with one equivalent of the dithiane.

The unfunctionalized sulfur of the compounds represented by formula III is selectively oxidized by reacting one molar equivalent of the mono-N-tosylsulfimide with two to four molar equivalents of 40% by weight peracetic acid in glacial acetic acid at about 20° to 30° C. to yield the corresponding sulfonyl/N-tosylsulfimide having the formula

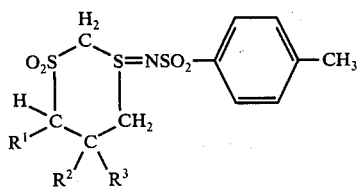
(IV)

wherein $R^1$, $R^2$, and $R^3$ have the same meaning given in formula I above.

Further oxidation of the compounds represented by formula IV to convert the tosylsulfimide substituent to tosylsulfoximide may be carried out by reacting one molar equivalent of the sulfonyl/N-tosylsulfimide compound with at least about one molar equivalent of potassium permanganate in acetic acid-acetic anhydride solution at about 20° to 30° C. The corresponding sulfonyl/N-tosylsulfoximide produced having the formula

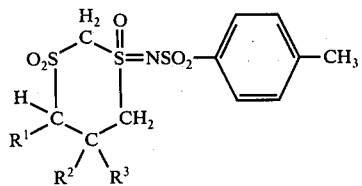
(V)

wherein $R^1$, $R^2$ and $R^3$ have the same meaning given in formula I above also may be synthesized directly from the compounds of formula III by reacting one molar equivalent of the mono-N-tosylsulfimide with about 6 to 7 molar equivalents of potassium permanganate in acetic acid-acetic anhydride solution at about 20° to 30° C.

The compounds represented by formula V when heated with a mineral acid, such as concentrated sulfuric acid at 25° to 90° C. yield the corresponding sulfonyl/sulfoximine having the formula

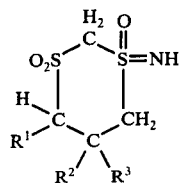 (VI)

wherein $R^1$, $R^2$ and $R^3$ have the same meaning given in formula I above. The compounds of formula VI also may be synthesized from the compounds of formula V by reacting one molar equivalent of the sulfonyl/N-tosylsulfoximide with about 3 to 5 molar equivalents of metallic sodium in liquid ammonia.

The sulfonyl/sulfoximines of formula VI are converted to the corresponding sulfonyl/N-alkylsulfoximines (VII) by heating the sulfonyl/sulfoximine and an alkylating agent, e.g., an alkylfluorosulfonate, in substantially equimolar amounts at reflux in a solvent, e.g., acetonitrile, to give the fluorosulfonate salt which is neutralized with, e.g., sodium bicarbonate, to give the said sulfonyl/N-alkylsulfoximines having the formula

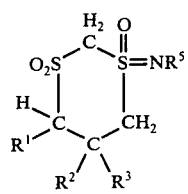 (VII)

wherein $R^5$ is alkyl, preferably lower alkyl having 1 to 4 carbon atoms and $R^1$, $R^2$ and $R^3$ have the same meaning given in formula I above.

The sulfonyl/sulfoximines of formula VI also may be converted to the corresponding sulfonyl/N-alkylsulfonylsulfoximides having the formula

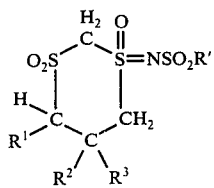 (VIII)

wherein R' is alkyl, preferably lower alkyl having 1 to 4 carbon atoms and $R^1$, $R^2$ and $R^3$ have the same meaning given in formula I above.

The compounds of formula VIII may be prepared in several ways:

Firstly, as further delineated in Example 9, the sulfonyl/sulfoximine as exemplified by 1-imino-1,3-dithiane-1,3,3-trioxide is reacted with methane sulfonyl chloride in the presence of an appropriate solvent such as pyridine. The resultant residue is concentrated, extracted and collected by known methods.

The second method of obtaining these compounds is by the Schotten Baumann reaction whereby the sulfoximine compound is placed in a dilute alkali to which resultant solution is added the acid chloride reagent, i.e., methane sulfonyl chloride.

The novel 2-substituted thioether compounds of the present invention also may be prepared in several ways and may be represented by the formula

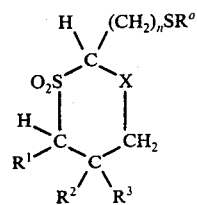 (IX)

wherein $R^o$ is an inert hydrocarbon radical, n is 0 or a positive integer other than 1 and $R^1$, $R^2$, $R^3$ and X have the same meaning given in formula I above.

These thioethers may be synthesized from the compounds of formulas IV to VIII by reaction with the appropriate alkylating agent, e.g., $R^oS(CH_2)_nCl$ to yield the corresponding 2-thioether derivatives. The thioether derivatives of the compounds of formulas VI to VIII also may be synthesized from the sulfonyl/N-tosylsulfoximides of formula V as exemplified by (4). In preparing the 2-thioether-substituted sulfonyl/sulfoximines of formula VI, the reaction is basically two-fold involving either initial alkylation with, e.g., $R^oS(CH_2)_nCl$ followed by cleavage of the end product or the alternative, i.e., initial cleavage followed by alkylation of the end product with, e.g., $R^oS(CH_2)_nCl$. This is to say that, however derived, the sulfonyl/N-tosylsulfoximide (4) is either alkylated to give the corresponding 2-thioether-substituted sulfonyl/N-tosylsulfoximide (10) which is cleaved to give the corresponding 2-thioether-substituted sulfonyl/sulfoximine (11) or, in the alternative, the sulfonyl/sulfoximide (4) is first cleaved to give the sulfonyl-sulfoximine (9) which in turn is alkylated to yield the corresponding thioether (11). The 2-thioether-substituted compounds of formulas VII and VIII as exemplified by (12) and (13), respectively, are prepared from the thioether-substituted sulfonyl/sulfoximines by reaction of the thioether derivatives of the sulfoximines as exemplified by (11) with an alkylfluorosulfonate and an alkane sulfonyl chloride, respectively.

These reactions may be exemplified as follows:

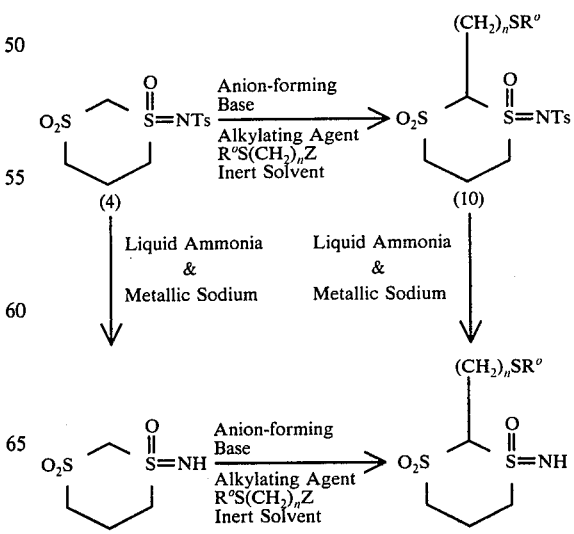

-continued

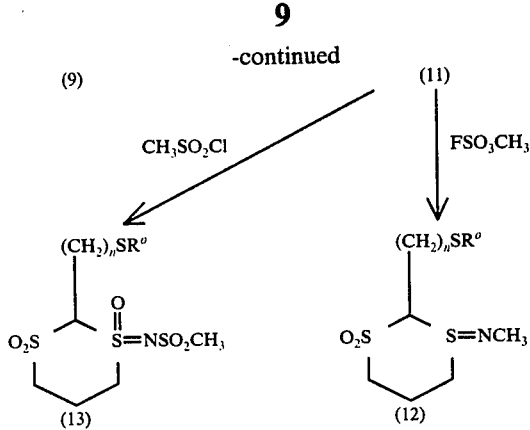

where Ts is

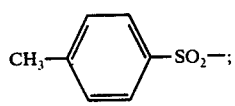

$n$ is 0 or a positive integer other than 1; $R^o$ is an inert hydrocarbon radical; and Z is halo or tosylate.

In a preferred embodiment, the thioether compounds of the present invention may be represented by the formula

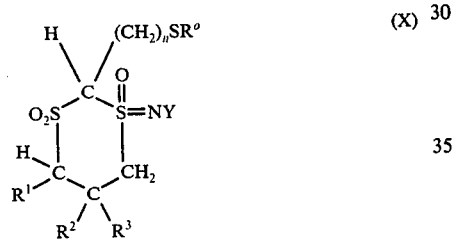
(X)

wherein $n$ is 0 or a positive integer other than 1, usually 0, 2, 3, 4 or 5 and preferably 0 or 2; $R^o$ is an inert hydrocarbon radical such as alkyl, aryl, cycloalkyl, alkylaryl, etc., preferably alkyl with 1 to 4 carbons, and Y is selected from hydrogen, alkyl, and $SO_2R^7$ where $R^7$ is alkyl or alkaryl, preferably alkyl with 1 to 4 carbon atoms or p-alkylphenyl wherein the alkyl has 1 to 4 carbon atoms and $R^1$, $R^2$ and $R^3$ have the same meaning as assigned in formula I above.

Specific examples of these thioether compounds useful as silver complexing agents in accordance with the present invention include, but are not limited to:

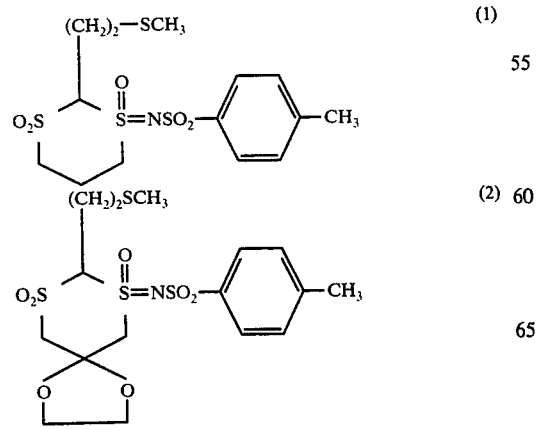

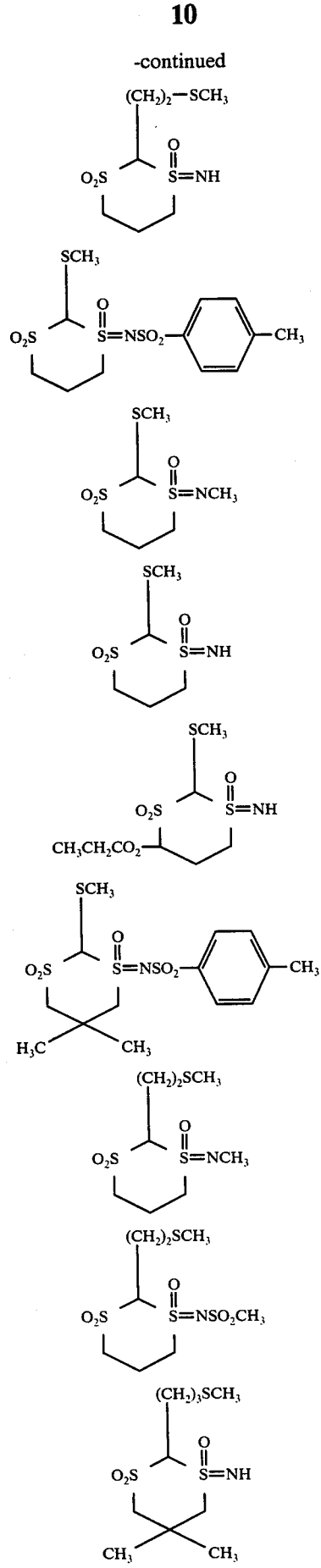

-continued

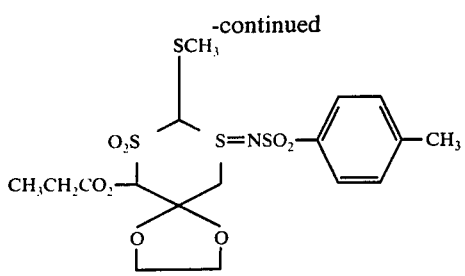
(12)

As discussed above, in preparing the thioether derivatives of the compounds of formula VI, the sulfonyl/N-tosylsulfoximides of formula V are used as "intermediates". As the above reaction sequence indicates, the "intermediate" may be either cleaved to form the corresponding sulfonyl/sulfoximine which is accordingly alkylated to obtain the corresponding thioether, or the "intermediate" may first be alkylated and then cleaved to obtain the same thioether.

Cleavage of the tosyl group from the sulfonyl/tosylsulfoximide is accomplished as mentioned earlier in this specification, either by heating with a strong mineral acid such as sulfuric acid or by treating with metallic sodium in liquid ammonia. The first synthetic example of a sulfoximine was prepared in 30% by weight yield by Whitehead and Bentley *J. Chem. Soc.*, 1950, p. 2081 by cleavage of the corresponding N-tosylsulfoximide with concentrated sulfuric acid. This method is still employed when it is not desirable to obtain sulfoximines directly by reaction of the appropriate sulfoxides with hydrazoic acid, see for example, Johnson and Schroeck, *J. Amer. Chem. Soc.*, 90, p. 6852 (1968) and Cram et al, ibid., 92, p. 7369 (1970). The application of sulfuric acid hydrolysis to the N-tosylsulfoximide (4) by Greenwald et al., *Tetrahedron Letters*, 1975, p. 3885, led to the isolation of the corresponding sulfoximine (9) in 20-30% by weight yield with considerable difficulty encountered in isolation and purification. An alternate procedure, which not only allows easier isolation but also scale-up, has now been developed. Thus treatment of (4) with sodium in liquid ammonia (4g-atoms sodium to 1 mole sulfoximide, 4 hr., −33°) gave an 85% by weight yield of (9). The generality of this procedure was demonstrated by obtaining dimethylsulfoximine in 50-60% by weight yield from the corresponding N-tosylsulfoximide, and the thioether compound of Example 18 from the corresponding tosylsulfoximide in 76% by weight yield. This method of cleavage forms the subject matter of copending application Ser. No. 784,669 of David H. Evans and Richard B. Greenwald filed Apr. 5, 1977.

In this method, the ratio of sodium to ammonia is not critical with the one proviso that there be a sufficient amount of the ammonia solvent to obtain a workable suspension. It is important, however, that an excess of metallic sodium be used in relation to the amount of tosylsulfoximide present. It has been established that not less than about 3 equivalents of metallic sodium per equivalent of tosylsulfoximide should be present; 4 or 5 equivalents of sodium being generally employed with greater than 5 equivalents being operative but unnecessary.

With respect to the alkylation procedure, whether again referring to alkylation of the compounds of formulas IV to VIII to form the corresponding 2-thioether-substituted compound or alkylation of the tosylsulfoximide in the alternate route to derive the novel thioethers, the concentration of alkylating agent to base is again not critical. The major consideration with regard to the concentration of the anion-forming base is that there be a sufficient amount of the solvent to provide a workable suspension. The concentration of alkylating agent on the other hand should be at least one equivalent per equivalent of tosylsulfoximide or compound of formulas IV or VI to VIII with a 10 to 30% excess generally employed.

In the alkylation reaction, the reactants and anion-forming base are taken up in an organic liquid which is a solvent for the reactants and which is itself inert to the reactants, for example, aprotic solvents with high dielectric constants such as dimethylformamide (DMF), dimethylsulfoxide, or hexamethylphosphoramide.

Once taken up into solution the suspension is preferably heated, the temperature not to exceed 100° C. While the reaction may occur at ambient temperatures, one runs the risk of the reactants coming out of solution in the interim. Generally speaking therefore, heating the reaction mixture to between about 40° and 80° C has been found to be adequate.

The reaction mixture is then usually allowed to cool after a color change has been noted, the solvent removed in vacuo and the residue triturated in the presence of, for example, methanol after which the composition is chilled and scratched to yield the product.

The following examples are given to further illustrate the present invention and are not intended to limit the scope thereof:

EXAMPLE 1

Preparation of the compound having the formula

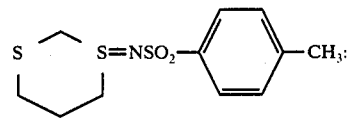

1,3-Dithiane (10 gms., 83.5 mmoles) was dissolved in about 75 mls. of methanol and the solution decanted from a small amount of insoluble material. A filtered solution of N-chloro-p-toluenesulfonamide sodium salt trihydrate (26 gms., 92 mmoles) in about 175 mls. of methanol was added to the dithiane solution. A copious white solid formed immediately upon the addition. The resulting mixture was heated at reflux for about 3 hours and allowed to stand at room temperature overnight. The precipitate was collected by filtration, triturated with water, collected and dried to give 17.6 gms. of the title compound, melting point 165° C. (recrystallized from water).

Analysis for $NS_3O_2C_{11}H_{15}$:

| | C | H | N | S |
|---|---|---|---|---|
| Calculated | 45.6 | 5.19 | 4.85 | 33.2 |
| Found | 46.07 | 5.37 | 4.48 | 33.17 |

EXAMPLE 2

Preparation of the compound having the formula

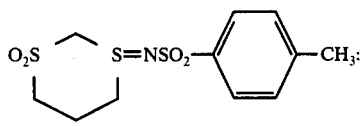

The mono-N-tosylsulfimide prepared in Example 1 (1 g., 3.46 mmoles) was dissolved in 20 mls. of freeze-dried glacial acetic acid by warming slightly to aid solution and then cooling to about 20° C. 40% peracetic acid (2.2 g.) in 5 mls. of glacial acetic acid was added dropwise to the solution over 5 minutes, and the reaction mixture was allowed to stand overnight. A white crystalline solid separated which was collected (0.5 g.), triturated with water and then recrystallized from about 50 mls. of hot water to give the title compound, melting range 187°–188° C.

Analysis for $NO_4S_3C_{11}H_{15}$:

|  | C | H | N | S |
|---|---|---|---|---|
| Calculated | 41.1 | 4.67 | 4.36 | 30.0 |
| Found | 41.23 | 4.77 | 4.48 | 29.73 |

EXAMPLE 3

Preparation of the compound having the formula

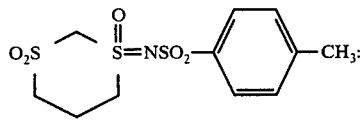

Potassium permanganate (0.87 g.) was partially dissolved in a mixture of 20 mls. glacial acetic acid/6 mls. acetic anhydride, and 0.2 g. of a macrocyclic polyether sold under the designation DC-18-Crown-6 was added resulting in the complete solution of the permanganate. The compound prepared Example 2 (0.8 g.) was added to the solution in portions. No exotherm was observed but a dark precipitate began to form and the reaction mixture began to turn brown. The reaction mixture was stirred at room temperature. After about 2 hours, the originally purple reaction mixture was predominantly brown, but after about 4 hours, essentially no purple color remained. Stirring was continued overnight, and the reaction mixture was filtered to give 0.3 g. of a beige solid, melting range 217°–22° C. (dec.). Recrystallization of the solid from 20 mls. of 1:1 ethanol/water containing Celite gave 60 mg. of the title compound, melting range 219°–221° C. (dec.).

Analysis for $NO_5S_3C_{11}H_{15}$:

|  | C | H | N | S |
|---|---|---|---|---|
| Calculated | 39.20 | 4.45 | 4.16 | 28.55 |
| Found | 39.33 | 4.46 | 4.27 | 28.55 |

EXAMPLE 4

Preparation of the compound having the formula

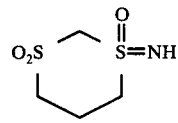

The compound prepared in Example 3 was taken up in conc. sulfuric acid, heated on a steambath for about 5 minutes, and filtered through a sintered filter to remove a small amount of insoluble material. The chilled amber filtrate was poured onto ice. A small amount of precipitate was collected and discarded, and the filtrate was carefully neutralized to pH 6 with sodium hydroxide. Celite was added and the solution was filtered to give a clear amber filtrate which was evaporated to dryness. The residue was extracted with boiling alcohol and filtered. The solution when cooled deposited a crystalline solid which was collected to give about 0.3 g. of the title compound, melting range 210°–213° C.

EXAMPLE 5

Preparation of the compound having the formula

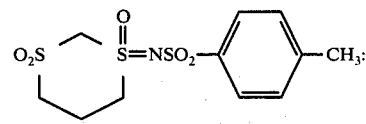

A partial solution of finely ground potassium permanganate (3.6 gms., 22.8 mmoles) in 25 mls. glacial acetic acid/8 mls. acetic anhydride was prepared in a 3-neck round bottom flask fitted with a mechanical stirrer and thermometer. The compound prepared in Example 1 (1 gm., 3.49 mmoles) was added to the stirred permanganate solution in portions so that the temperature did not exceed 35° C. Stirring was continued at ambient temperature for about 2 days. The reaction mixture was then filtered by suction giving a pinkish brown solid which was suspended in water, decolorized with sulfur dioxide and collected to yield 0.75 gm. of the title compound as an off-white solid, melting range 217°–220° C. (dec.).

EXAMPLE 6

Preparation of the compound having the formula

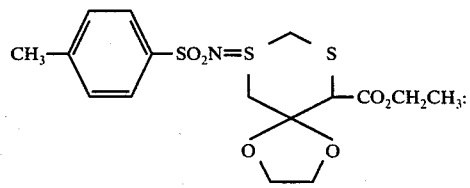

N-chloro-p-toluenesulfonamide sodium salt trihydrate 12.4 gms. 44 mmoles) was dissolved in 250 mls. of ethanol with slight warming and the resulting solution filtered. The 1,3-dithiane,

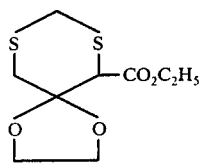

(10g., 40 mmoles), in 10 mls. of ethanol was added to the chloramine T solution, and the reaction mixture was stirred at room temperature for about 2.5 hours then at reflux for 1 hour. White solid separated which was collected by filtration after cooling the reacting mixture to room temperature. The filtrate was concentrated to half-volume and allowed to stand overnight. The insoluble white material was collected, triturated with water and combined with the white solid previously collected to give 8.1 g. of the title compound which upon crystallization from alcohol showed a melting range of 153°–155°.

It will be appreciated that the compound prepared in Example 6 may be selectively oxidized to the corresponding sulfonyl/N-tosylsulfimide and/or to the corresponding sulfonyl/N-tosylsulfoximine using the procedures described above and also that the sulfonyl/N-tosylsulfoximide thus formed may be converted to the corresponding sulfonyl/sulfoximine and the corresponding sulfonyl/N-alkylsulfoximine as described above.

EXAMPLE 7

Preparation of the compound having the formula

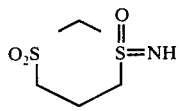

Sodium metal (3.42 g., 149 mmoles) was added over the course of 1.5 hours to a suspension of the compound of Example 3 (10 g., 29.8 mmoles) in about 100 mls. of liquid ammonia in a dry ice/acetone bath. The reaction mixture was stirred in the cooling bath for about one hour, removed from the bath, refluxed for three hours and allowed to evaporate in the hood overnight. The reaction mixture was then warmed moderately in a water bath under a stream of nitrogen and chilled in an ice bath. About 100 mls. of cold water was added, dropwise initially, and the solution was filtered by suction to remove a small amount of pasty brown solid, adjusted to a pH of about 6.5 with concentrated HCl, chilled and was filtered to remove a small amount of white solid. The filtrate was stripped to dryness on a rotary evaporator and the white residue was boiled for 5 minutes with approximately 100 mls. of ethanol. The supernatant was decanted through a suction filter, and the residue was extracted with 50 mls. additional ethanol. The filtrate turned cloudy on cooling, and after about two hours, it was filtered by gravity and stripped. The residue was reextracted with 100 mls. of hot ethanol to give 1.5 g. of the title compound (melting range 214°–216° C. after recrystallization from acetonitrile).

|  | Analysis for $C_4H_9NO_3S_2$ | | |
| --- | --- | --- | --- |
|  | C | H | N |
| Calculated | 26.20 | 4.91 | 7.65 |

|  | Analysis for $C_4H_9NO_3S_2$ | | |
| --- | --- | --- | --- |
|  | C | H | N |
| Found | 26.42 | 4.94 | 7.62 |

EXAMPLE 8

Preparation of the compound having the formula

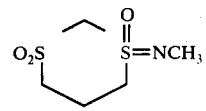

The compound of Example 7 (1.8 g., 7.7 mmoles) was dissolved in 45 mls. of acetonitrile and the resulting pale amber solution was dried over magnesium sulfate, filtered and transferred to a flame-dried assembly under a drying tube. Methylfluorosulfonate (0.88g., 7.7 mmoles) was added to the solution in one portion and the resulting reaction mixture was heated quickly to reflux. After refluxing for about 0.5 minute, the reaction mixture was allowed to cool. A turbidity developed and a gummy solid began to separate. After about 15 minutes, the reaction mixture was cooled in an ice bath. There was no appreciable increase in the amount of precipitate. The solvent was removed in vacuo to give an amber syrup which was triturated with ether to give a sticky glass. The ether was decanted, and the residue was taken up in 25 mls. of cold water, neutralized with 5% sodium bicarbonate (about 30 mls.) and extracted overnight with chloroform. The amber extract was dried over magnesium sulfate and stripped to give 0.8 g. of the title compound as an amber solid (melting range 201°–204° C. after recrystallization from isopropanol).

EXAMPLE 9

Preparation of the compound having the formula:

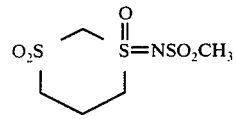

A suspension of 1-imino-1,3-dithiane-1,3,3-trioxide (as prepared in Example 4) (2.2g., 12.0 m moles) in pyridine (40 ml.) was chilled in an ice bath. Methanesulfonylchloride (1.52 g., 13.2 m moles) was added dropwise to the suspension over a 5 to 10-minute period. After all of the methanesulfonylchloride was added, the ice bath was removed and the reaction was allowed to attain room temperature while being stirred for about 24 hours. During the first hour of the 24-hour period a pale yellow color developed, the reaction mixture became increasingly more homogeneous; and by the end of this 24-hour period, a white solid had separated from the solution. The reaction mixture was concentrated on a rotary evaporator and the resultant pasty residue was readily dissolved in water.

The pH of the aqueous solution of residue was made slightly acidic by the addition of hydrochloric acid. The solid that separated was collected to give 1.7 g. of the title compound (melting range of 159°–162° C).

Crystallization from water afforded an analytical sample.

| Analysis for NO₅S₃C₅H₁₁: | | | |
|---|---|---|---|
| | C | H | N |
| Calculated | 23.00 | 4.22 | 5.36 |
| Found | 22.89 | 4.24 | 5.49 |

EXAMPLE 10

Preparation of the compound having the formula:

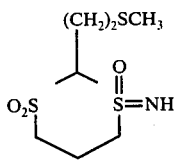

Two grams (2.0 g., 10.9 m moles) of 1-imino-1,3-dithiane-1,3,3-trioxide (as prepared in Example 4) and potassium carbonate (1.66 g., 12 m moles) were suspended in dimethylformamide (20 mls.) hereinafter referred to as DMF. To the suspension was added β-chloroethyl-methylsulfide (1.32 g., 12.0 m moles). The suspension was maintained at 80° C for approximately 16 hours with a pale yellow color becoming more evident as heating continued.

At the completion of the 16-hour period, 0.3 g. of β-chloroethyl-methylsulfide was added to the heated suspension and the same was maintained at 80° C for an additional 5 hours. The suspension was allowed to cool and stand overnight. The solvent was removed in vacuo, and the residue was taken up in water (about 40 ml.). The solution was extracted with methylenechloride (50 ml.) and extracted a second time in the same manner. The extract was dried over magnesium sulfate and thereafter stripped to give 2 grams of the title compound.

EXAMPLE 11

Preparation of the compound having the formula:

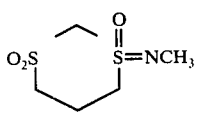

The procedure followed in Example 8 was repeated as follows. A suspension of 1-imino-1,3-dithiane-1,3,3-trioxide (as prepared in Example 7) (4.1 g., 22.4 m moles) in acetonitrile (150 ml.) was heated quickly to reflux with a heating gun. Methylfluorosulfonate (2.72 g., 24.7 m moles) was added in its entirety and the suspension was again heated quickly to initiate reflux. The suspension was heated to sustain reflux for approximately 60 seconds after which the reaction mixture was allowed to cool slowly to room temperature for about 1 hour. The suspension was then filtered and the solvent stripped on a rotary evaporator. The amber-colored taffy-like residue was taken up in water (40 ml.) to give a cloudy solution. "Celite", a filter aid manufactured by Johns Manville and containing diatomaceous earth was added to the solution in order to remove the impurities and the solution was again filtered to give a pale yellow solution. The pH of the solution was adjusted to about 6.5 using a 5% solution of sodium bicarbonate (about 43 mls.). The solution was then extracted continuously with chloroform for a period of 48 hours and the chloroform extract was thereafter dried over magnesium sulfate.

The solvent was stripped from the residue and the resultant dry solid triturated with about 20 ml. ethanol-2B (anhydrous ethanol denatured with benzene) to give an off-white solid which was collected to give about 1 g. of the title compound (melting range 204°–206.5° C).

EXAMPLE 12

Preparation of the compound having the formula:

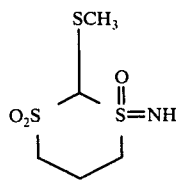

One gram (1 g.) of 1-imino-1,3-dithiane-1,3,3-trioxide (as prepared in Example 4) was dissolved in dimethylformamide (10 ml.) to give a colorless solution. To this solution was added, in one portion, potassium carbonate (0.755 g., 5.46 m moles). One equivalent of methylthiotosylate (1.1 g., 5.46 m moles) was then added to the reaction mixture which was heated to about 80° C. After maintaining the mixture at this temperature for about 2 hours, the reaction mixture became homogeneous and darkened somewhat in color. However, on evaluation by thin layer chromatography (TLC) there was evidence of unconverted starting material being present. Therefore, the reaction mixture was again heated to 80° C and maintained at that temperature overnight (about 16 hours). On further evaluation by TLC only a very minor amount of unconverted starting material remained.

The solvent was then removed in vacuo yielding the title compound as a white solid material (melting range 172° C–173° C.

EXAMPLE 13

Preparation of the compound having the formula:

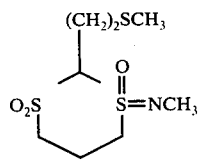

1-methylimino-1,3-dithiane-1,3,3-trioxide (as prepared in Example 8) (1.97 g., 10 m moles) was placed in a glass assembly which had been flame-dried and allowed to cool to ambient temperature and then dissolved in 20 ml. DMF by briefly warming to about 45° C. Potassium t-butoxide [1.27 g., 11.5 m moles (× 1.15)] was added to the solution which resulted in little color change in the amber solution. The solution was stirred at ambient temperature for about 30 minutes and β-chloroethyl-methylsulfide (1.27 g., 11.5 m moles) in dimethylformamide (5 ml.) was added dropwise over a period of about 14 minutes. The temperature of the solution was thereafter raised to about 75° C and maintained at that temperature for about 16 hours. A white solid separated. On evaluation of the supernatant by TLC using 10% methanol/chloroform on silica gel, the supernatant proved to be largely homogenous with only a small amount of unconverted starting material being present. β-chloroethyl-methylsulfide (0.15 g.) was again added to the reaction mixture which was then heated at 75° C for an additional 3 hours. The reaction mixture was cooled and the solvent stripped on a rotary evaporator after adding a small amount of water. Even less unconverted starting material was then noted. The residue was taken up in water (50 ml.) and thereafter extracted with chloroform in two portions of 40 mls. each. The amber extract was dried over magnesium sulfate and thereafter stripped to obtain a amber-colored syrup.

The syrup retained its syrupy consistency after having been allowed to stand for 72 hours at ambient temperature. The syrup was triturated with several portions of ether which caused the syrup to be converted to a taffy-like consistency. The taffy-like residue was triturated with petroleum ether to give the title compound as a beige-colored solid (melting range of 112°–114° C).

EXAMPLE 14

This is a preferred procedure of preparing the compound of Example 10 due in part to the more nearly pure form of the title compound derived.

A suspension of 1-imino-1,3-dithiane-1,3,3-trioxide (as prepared in Example 4) (737 mg., 4.02 m moles) and potassium carbonate (570 mg., 4.1 m moles) was prepared in dimethylformamide (7.5 ml.). To the suspension was added β-chloroethyl-methyl sulfide (460 mg., 4.1 m moles). The suspension was heated to 70° C, and a pale yellow color developed. The suspension was maintained at this temperature for about 4 hours with no darkening of the color being evident.

The temperature was then raised to 80° C and maintained at that temperature for 2 hours. The suspension was allowed to cool to ambient temperature. The suspension was stirred continuously at this temperature over the weekend (about 64 hours) at which time the suspension still exhibited a pale yellow color.

β-chloroethyl-methyl sulfide (138 mg.) was again added to the suspension and heating of the same was resumed at about 75° C. The suspension was maintained at this temperature for 4 hours with a lessening of the amount of unconverted starting material being noted at that time. The reaction mixture was poured into water, and a gummy substance separated out. This was extracted two times with chloroform (35 ml. ea.) and the extract was thereafter dried over magnesium sulfate. The dried extract was then stripped to give a slightly sticky solid (about 1 g.) which was triturated with ethanol-2B (10 ml.) to give approximately 0.2 g. of the title compound as a white needle-like solid (melting range of 163°–166° C).

EXAMPLE 15

This is an additional procedure of preparing the compound of Example 12.

1-imino-1,3-dithiane-1,3,3-trioxide (0.5 g., 2.74 m moles) and potassium carbonate (0.38 g., 2.74 m moles) were taken up in dimethylformamide (10 ml.). Methyl thiotosylate (0.56 g., 2.77 m moles) was added to the suspension and the same heated to 80° C to give a colorless solution. Within 30 minutes, at this temperature, a solid commenced to precipitate from the hot reaction mixture. Heating of this mixture at 80° C was continued for about 2 hours during which time a pale amber color developed. The reaction mixture was maintained at 80° C for an additional 6 hours and then was allowed to stand at room temperature for about 64 hours. The solvent was removed in vacuo to give a yellow solid which was soluble at a pH of about 8.

The solid was triturated with methanol, chilled and scratched to give a white solid. The solid was triturated once again but with water (3 ml.) to yield the title compound as a white solid (melting range of 172°–173° C).

EXAMPLE 16

Preparation of the compound having the formula:

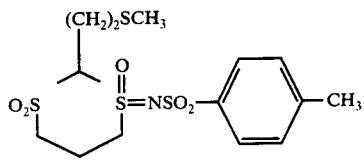

The compound 1-tosylimino-1,3-dithiane-3,3-dioxide (as prepared in Example 2) (10 g., 29.6 m moles) was readily dissolved in dimethylformamide (100 ml.), the solution having been placed in a flame-dried 500 ml. round-bottom 3-neck flash fitted with a thermometer, dropping funnel and a nitrogen inlet. Potassium t-butoxide [3.65 g., 32.6 m moles (× 1.1)] was added with a spatula to the dimethylformamide solution over a 2-minute period. A green color developed which rapidly changed to a dark steel blue.

The suspension was stirred for one hour at ambient temperature and β-chloroethyl-methyl sulfide (3.6 g., 32.6 m moles) was thereafter added to the suspension dropwise over a 10-minute period. The blue color was largely dissipated to give a dark tan-colored reaction mixture. The mixture was then stirred for 1.5 hours at ambient temperature after which the temperature was raised to 70° C. The mixture was maintained at that temperature for approximately 16 hours during which time the color of the reaction mixture lightened with some separation of solid.

On evaluation by thin layer chromatography at this stage of the reaction using 10% methanol/chloroform on silica gel a minor amount of unconverted starting material was found to be present.

The reaction mixture was allowed to cool and was then poured into cool water. The gummy precipitate was extracted with chloroform which extract was thereafter washed thrice with water (200 ml. per washing). The extract was then dried over magnesium sulfate and stripped to give an amber syrup. The syrup was triturated with several portions of ether to give a solid residue (9.4 g.) which was taken up in boiling ethanol-2B (100 ml.) in which the residue was not entirely soluble to give a white granular solid. This was allowed to stand for about 72 hours. The solid was collected to give 7.3 g. of the title compound (melting range 112°–118° C).

EXAMPLE 17

The same compound as prepared in Example 12 was synthesized by the following procedure which is a variation of that method employed previously.

1-imino-1,3-dithiane-1,3,3-trioxide (3.0 g., 16.4 m moles) was dissolved in dimethylformamide (50 ml.). To this solution was added potassium carbonate (2.3 g., 16.7 m moles) and methylthiotosylate (3.8 g., 18.8 m moles). The entire suspension was heated for 16 hours at about 80° C. An amber color developed and separation of solids from the reaction mixture was noted. On evaluation by thin layer chromatography (TLC) there was evidence of some unconverted starting material with essentially no methylthiotosylate being present.

An additional 25% of methylthiotosylate and potassium carbonate was added to the reaction mixture and the latter again was heated to 80° C for about 5 hours. On evaluation by TLC, the amount of unconverted starting material had appreciably diminished.

The reaction mixture was allowed to cool and stand for about 16 hours, after which the solvent was stripped from the mixture following the addition of a small amount of water.

The residue was triturated with methanol (30 ml.), chilled and scratched to yield 2.5 g. of the title compound as a white solid (melting range of 172°–173° C).

EXAMPLE 18

Preparation of the compound having the formula:

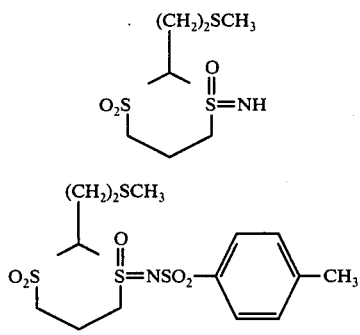

Compound A

Compound A (1.5 g., 3.54 m moles) was added to liquid ammonia (30 ml.) in a 3-neck flask fitted with a dry-ice condenser and a drying tube. A very pale yellow partial solution resulted. Sodium spheres (0.35 g. in toto; 14.6 m moles) were added to the solution in portions over a 20-minute period. A transient green-blue color formed near the dissolving sodium. When the addition of the sodium spheres was complete, a lemon yellow suspension resulted.

The yellow suspension was maintained at a slow reflux under the condenser for about 2 hours and was then allowed to evaporate over a 16-hour period. It was noted that after about 30 minutes of reflux time the yellow color was almost dissipated and disappeared after one hour.

The resultant cream-colored residue was taken up in water (30 ml.) to give a pale yellow solution. The solution was filtered to remove a small amount of flocculant material which solution was then neutralized to a pH of 6–7; about 2 ml. of concentrated hydrochloric acid was required. The pH-adjusted solution was cloudy and remained slightly cloudy after being filtered. The solution was stripped on a rotary evaporator to give a granular white solid.

On examination by TLC using 10% methanol/chloroform on silica gel, no unconverted starting material remained. The crude residue was boiled in acetonitrile and thereafter filtered to remove the insoluble materials. On evaluation by TLC, the remaining composition was largely homogenous. The residue (0.7 g.) was dissolved in hot acetonitrile (about 18 ml.) and allowed to stand. 0.7 g. of the title compound was collected (melting range of 165°–167.5° C).

EXAMPLE 19

Preparation of the compound having the formula:

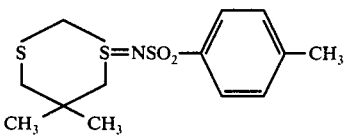

A. To a solution of boron trifluoride etherate (5 ml.), acetic acid (10 ml.) and 150 ml. of chloroform in a dry 500 ml. three-necked round-bottomed flash fitted with mechanical stirrer, coil condenser and non-pressure equalizing dropping funnel, 2,2-dimethyl-1,3-propane dithiol[1] (5.7 g., 42 m moles) and dimethoxymethane (3.5 g., 46 m moles) were added according to the method of Corey and Seebach[2]. Workup following the described procedure afforded crude 5,5-dimethyl-1,3-dithiane as a pale yellow liquid (6.1 g., 98%) which was homogeneous by TLC (silica gel/benzene). ($CDCl_3$): $\delta$ 1.15 (S,6H); 2.86 (S,4H); 3.58 (S,2H).

(1) E. L. Eliel, U. S. Rao, S. Smith and R. O. Hutchins, *J. Org. Chem.*, 40, 525 (1975).
(2) E. J. Corey and D. Seebach, *Organic Syntheses*, 50, 72 (1970).

B. To a stirred methanolic solution (25 ml.) of 5,5-dimethyl-1,3-dithiane (1 g., 6.75 m moles) Chloramine T trihydrate (2.3 g., 8.1 m moles) was added in portions over 5 minutes. White solid began to separate after 5 minutes. The reaction mixture was stirred for 1.5 hours at ambient temperatures then poured into 75 ml. of water and stirred for 5 minutes. The homogeneous solid was collected and dried (1.9 g., 89%), melting range 187°–190° C. An analytical sample was obtained by crystallization from ethanol-2B to yield 1 g. (15 ml.) of the title compound (melting range of 188°–190° C). Calculated for $C_{13}H_{19}NO_2S_3$: C 49.16; H 5.99; N 4.42; Found: C 49.24; H 5.94; N 4.38.

EXAMPLE 20

Preparation of the compound having the formula:

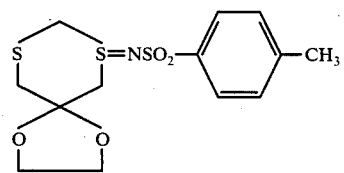

A solution of 5-oxo-1,3-dithiane dimethylene ketal (1 g., 6.2 m moles) prepared according to the method of Howard and Lindsey[1] was treated with Chloramine T trihydrate (2.1 g., 7.4 m moles) in portions over a 10-minute period. The reaction mixture was allowed to stir for 2 hours at ambient temperatures and then poured into 150 ml. of cold water. The precipitated solid was collected, washed and dried over magnesium sulfate to give the title sulfimide (1.3 g., 62% yield). Crystallization from ethanol-2B (1 g./40 ml.) afforded an analytical sample demonstrating a melting range of 185° C–187° C. Calculated for $C_{13}H_{17}NO_4S_3$: C 45.00; H 4.89; N 4.04; Found: C 45.06; H 4.99; N 4.07.

(1) E. G. Howard and R. V. Lindsey, Jr., *J. Amer. Chem. Soc.*, 82, 158 (1960).

The starting 1,3-dithianes may be prepared according to the procedures described in The Chemistry of the Heterocyclic Compounds, Vol. 21, part 2, p. 952 D. S. Breslow and H. Skolnik, John Wiley, 1966 and by E. G. Howard and R. V. Lindsey, Jr., J. Amer. Chem. Soc., Vol. 82, p. 158 (1960) and also may be prepared by reacting a dithiol of the formula,

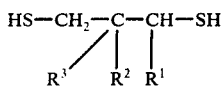

wherein $R^1$, $R^2$, and $R^3$ have the same meaning given above, and dimethoxy methane. As an illustration 5,5-dimethyl-1,3-dithiane was prepared as follows:

A solution of 10 mls. of acetic acid and 5 mls. of boron trifluoride etherate in 50 mls. of chloroform was heated to reflux in a 500 ml. 3-neck round bottom flask fitted with a mechanical stirrer, coil condenser and non-pressure equalizing addition funnel. A solution of 2,2-dimethyl-1,3-propanedithiol (5.7 g., 42 mmoles) and dimethoxymethane (3.5 g., 46 mmoles) in 100 mls. chloroform was added very slowly dropwise ($\Delta t \sim 3$ hours) to the acetic acid/boron trifluoride etherate solution. The reaction mixture was heated for two hours, cooled and allowed to stand at room temperature overnight. It was then washed with $3 \times 50$ mls. water, $2 \times 40$ mls. of 10% aqueous potassium hydroxide and $2 \times 50$ mls. of water to neutrality, dried over potassium carbonate and stripped on a rotary evaporator to give 6.2 g. of the title compound as a pale yellow liquid.

As mentioned previously, the novel compounds of the present invention as represented in formula I are useful as silver halide complexing agents. For example, the stability constant ($\beta_2$) for the silver complexes of the compounds of Examples 2, 3 and 4 as determined potentiometrically in 0.1 molar alkali were $2 \times 10^{12}$, $2 \times 10^{13}$ and $5 \times 10^{14}$, respectively, as compared to a $\beta_2$ stability constant of $1.2 \times 10^{12}$ for the silver complex of uracil, a conventional complexing agent for silver halide. The stability constants were determined by the Leden method as modified by Fronaeus (Ahrland, et al., J. Chem. Soc., 1958, p. 264).

Silver halide complexing agents have been used in various photographic products and processes, for example, as silver halide solvents, and photographic processing compositions capable of forming water-soluble complex silver salts are known to be useful in many types of silver halide photography. To obtain a relatively stable image in an exposed and developed photosensitive silver halide emulsion, the silver halide remaining in the unexposed and undeveloped areas of the emulsion should be converted to a soluble silver complex that can be removed by washing or converted to a stable silver complex that will not "print-out" upon prolonged exposure to light. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photographic processes. Such processes are now well known in the art; see for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

Silver halide solvents also have been employed in diffusion transfer processes adapted to provide positive silver transfer images which may be viewed as positive transparencies without being separated from the developed negative silver image including such processes adapted for use in forming additive color projection positive images. Diffusion transfer processes of this type are described in U.S. Pat. Nos. 3,536,488 of Edwin H. Land and 3,615,428 of Lucretia J. Weed and in U.S. application Ser. No. 383,196 of Edwin H. Land filed July 27, 1973, now U.S. Pat. No. 3,894,871. Silver halide solvents also find utility in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489 of Ronald F. W. Cieciuch, Roberta R. Luhowy, Frank A. Meneghini and Howard G. Rogers. The compounds of formula I find particular utility in the latter process, though compounds may be selected for use in other of the aforementioned processes as well.

The following examples are presented to illustrate the utility of the subject compounds as silver halide complexing agents in photography.

EXAMPLE I

A photosensitive element using, as the magenta dye,

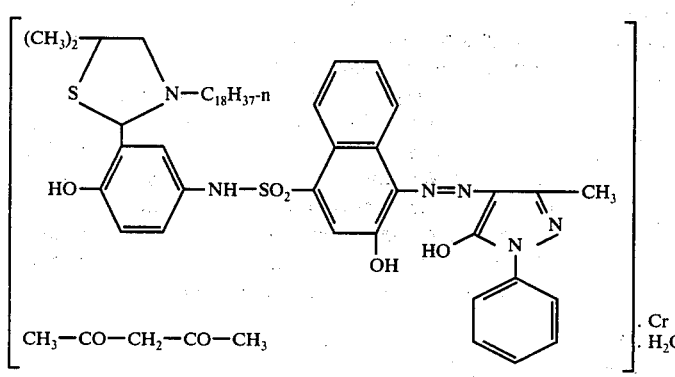
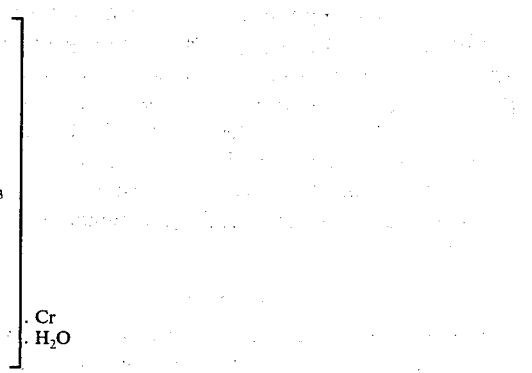

was prepared by coating a gelatin-subcoated 4 mil opaque polyethylene terephthalate film base with the following layers:

1. a layer of magenta dye dispersed in gelatin and coated at a coverage of about 70 mgs/ft$^2$ of dye and about 50 mgs/ft$^2$ of gelatin;
2. a gelatino silver iodochlorobromide emulsion containing 0.5 mg. KBr per gram of emulsion coated at a coverage of about 20 mgs/ft$^2$ of silver and about 60 mgs/ft$^2$ of gelatin; and
3. a layer of gelatin coated at a coverage of about 30 mgs/ft$^2$ of gelatin.

A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs/ft$^2$;
2. a timing layer containing about a 40:1 ratio of a 60-30-4-6 copolymer of butylacrylate, diacetone acrylamide, styrene and methacrylic acid and polyacrylamide at a coverage of about 500 mgs./ft.$^2$; and
3. a polymeric image-receiving layer containing a 2:1 mixture, by weight, of polyvinyl alcohol and poly-4-vinylpyridine, at a coverage of about 300 mgs./ft.$^2$ The two components thus prepared were then taped together to provide an integral film unit, with a rupturable container retaining an aqueous alkaline processing solution fixedly mounted on the leading edge of each of the components, by pressure-sensitive tapes, so that, upon application of compressive pressure to the container to rupture the container's marginal seal, its contents would be distributed between the image-receiving layer and the gelatin overcoat layer of the photosensitive component. The aqueous alkaline processing composition comprised:

| Water | 100 | cc. |
|---|---|---|
| Sodium hydroxide | 5.0 | g. |
| Carboxymethyl hydroxy-ethyl cellulose | 3.4 | g. |
| Tetramethyl reductic acid | 6.0 | g. |
| Sodium sulfite | 2.0 | g. |
| Titanium dioxide | 50.0 | g. |
| Compound of Example 8 | 0.56 | g. |

The photosensitive element was exposed through the transparent support and the layers thereon to a step-wedge and a layer approximately 0.0020 inch thick of the processing composition was distributed by passing the film unit between a pair of pressure-applying rolls in the dark. The resulting laminate was maintained intact to provide a color integral negative-positive reflection print, and after about 10 minutes in the dark, the maximum and minimum reflection densities were measured for the positive magenta image. The maximum reflection density obtained was 1.75 and the minimum reflection density was 0.30.

EXAMPLE II

Example I was repeated using the same photosensitive and image-receiving components and the same processing composition except that 0.50 g. of the compound of Example 7 was substituted for the 0.56 g. of the compound of Example 8. The maximum and minimum reflection densities measured after 10 minutes in the dark were 1.80 and 0.18, respectively.

EXAMPLE III

A photosensitive element using the same magenta dye as in Example I was prepared by coating a gelatin-subcoated 4 mil opaque polyethylene terephthalate film base with the following layers:

1. a layer of magenta dye dispersed in gelatin and coated at a coverage of about 50 mgs/ft$^2$ of dye and about 50 mgs/ft$^2$ of gelatin;
2. a gelatino silver iodochlorobromide emulsion containing 5 mgs KBr per gram of emulsion coated at a coverage of about 20 mgs/ft$^2$ of silver and about 60 mgs/ft$^2$ of gelatin; and
3. a layer of gelatin coated at a coverage of about 30 mgs/ft$^2$ of gelatin.

The photosensitive element thus prepared and an image-receiving element identical to that used in Example I were taped together to provide an integral film unit, with a rupturable container retaining an aqueous alkaline processsing solution fixedly mounted on a leading edge of each of the components, by pressure-sensitive tapes, so that, upon application of compressive pressure to the container's marginal seal, its contents would be distributed between the image-receiving layer and the gelatin overcoat layer of the photosensitive component. The aqueous alkaline processing composition comprised:

| Water | 100 | cc. |
|---|---|---|
| Sodium hydroxide | 5.0 | g. |
| Carboxymethyl hydroxy-ethyl cellulose | 3.4 | g. |
| Tetramethyl reductic acid | 6.0 | g. |
| Sodium sulfite | 2.0 | g. |
| Titanium dioxide | 50.0 | g. |
| Compound of Example 8 | 0.50 | g. |

The photosensitive element was exposed through the transparent support and the layers thereon to a step-wedge, and a layer approximately 0.0020 inch thick of the processing composition was distributed by passing the film unit between a pair of pressure-applying rolls in the dark. The resulting laminate was maintained intact to provide a color integral negative-positive reflection print, and after about 10 minutes in the dark, the maximum and minimum reflection densities were measured for the positive magenta image. The maximum reflection density obtained was 1.62 and the minimum reflection density was 0.33.

EXAMPLE IV–XI

Example III was repeated using the same photosensitive and image-receiving components and the same processing composition except that the compounds listed in the following table were employed in the processing composition on a molecular equivalent basis to the Compound of Example 8. The maximum and minimum reflection densities measured after 10 minutes in the dark were Table

| Compound | $D_{max}$ | $D_{min}$ |
|---|---|---|
| O₂S⟨⟩S=NSO₂—C₆H₄—CH₃ | 0.52 | 0.17 |
| O₂S⟨⟩S(=O)=NSO₂—C₆H₄—CH₃ | 1.38 | 0.33 |
| O₂S⟨⟩S(=O)=NH | 1.38 | 0.34 |
| O₂S⟨⟩S(=O)=NSO₂CH₃ | 0.89 | 0.25 |
| O₂S⟨(CH₂)₂SCH₃⟩S(=O)=NSO₂—C₆H₄—CH₃ | 0.36 | 0.15 |
| O₂S⟨(CH₂)₂SCH₃⟩S(=O)=NH | 1.05 | 0.15 |
| O₂S⟨SCH₃⟩S(=O)=NH | 0.99 | 0.16 |
| O₂S⟨(CH₂)₂SCH₃⟩S(=O)=NCH₃ | 0.49 | 0.16 |

EXAMPLE XII

A photosensitive silver iodobromide emulsion on a support was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding the compound of Example 8 in a concentration of 5% by weight to the following formulation:

| | |
|---|---|
| Water | 814.0 g. |
| Potassium hydroxide (Aqueous 50% 2/2 solution) | 348.0 g. |
| Hydroxyethyl cellulose | 35.0 g. |
| Zinc acetate | 15.0 g. |
| Triethanolamine | 5.6 g. |
| Bis-N,N-methoxyethyl hydroxylamine | 50.0 g. |

After an imbibition period of approximately one minute, the developed silver halide emulsion was separated from the image-receiving element, and the maximum and minimum transmission densities were measured for the positive silver image. The maximum density obtained was 1.56 and the minimum density was 0.44.

Since certain changes may be made in the above compositions and processes without departing from the scope of the invention herein involved, it is intended that all matter contained in the above description should be interpreted as illustrative and not in a limiting sense.

What is claimed is:
1. A compound of the formula

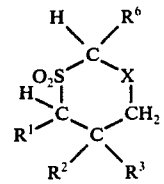

wherein $R^1$ is selected from hydrogen, alkyl containing 1 to 4 carbon atoms and $-CO_2R^4$ wherein $R^4$ is alkyl containing 1 to 4 carbon atoms; $R^2$ and $R^3$ when taken individually are selected from hydrogen and alkyl containing 1 to 4 carbon atoms and $R^2$ and $R^3$ when taken together are spiro; $R^6$ is selected from hydrogen and $-(CH_2)_nSR^0$ wherein $n$ is 0, 2, 3, 4 or 5 and $R^0$ is alkyl containing 1 to 4 carbon atoms and X is selected from

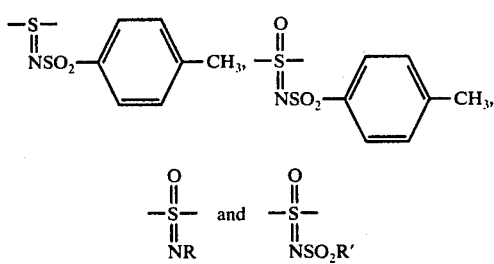

wherein R is hydrogen or alkyl containing 1 to 4 carbon atoms and R′ is alkyl containing 1 to 4 carbon atoms.

2. A compound as defined in claim 1 wherein $R^6$ is hydrogen.

3. A compound as defined in claim 2 wherein $R^1$ is alkyl.

4. A compound as defined in claim 2 wherein $R^1$ is $CO_2R^4$.

5. A compound as defined in claim 2 wherein $R^1$ is hydrogen.

6. A compound as defined in claim 2 wherein $R^2$ and $R^3$ are spiro [1,3-dioxolane-2].

7. A compound as defined in claim 2 wherein $R^2$ and $R^3$ are hydrogen.

8. A compound as defined in claim 2 wherein $R^2$ and $R^3$ are alkyl.

9. A compound as defined in claim 2 wherein X is

10. A compound as defined in claim 2 wherein X is

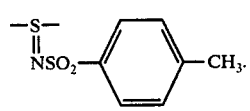

11. A compound as defined in claim 2 wherein X is

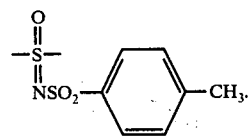

12. A compound as defined in claim 2 wherein X is

13. A compound as defined in claim 1 wherein $R^6$ is $-(CH_2)_nSR^0$.

14. A compound as defined in claim 13 wherein $R^1$ is hydrogen.

15. A compound as defined in claim 13 wherein $R^1$ is alkyl.

16. A compound as defined in claim 13 wherein $R^1$ is $CO_2R^4$.

17. A compound as defined in claim 13 wherein $R^2$ and $R^3$ are hydrogen.

18. A compound as defined in claim 13 wherein $R^2$ and $R^3$ are alkyl.

19. A compound as defined in claim 13 wherein $R^2$ and $R^3$ are spiro [1,3-dioxolane-2].

20. A compound as defined in claim 13 wherein X is

21. A compound as defined in claim 13 wherein X is

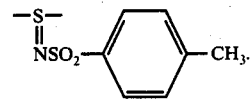

22. A compound as defined in claim 13 wherein X is

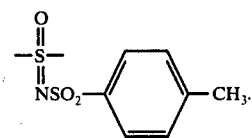

23. A compound as defined in claim 13 wherein X is

24. The compound

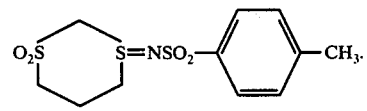

25. The compound

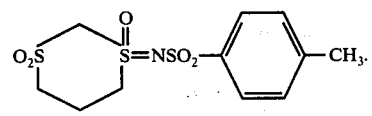

26. The compound

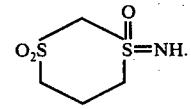

27. The compound

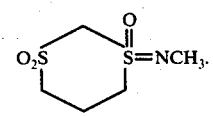

28. The compound

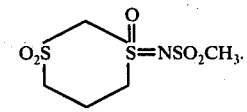

29. The compound

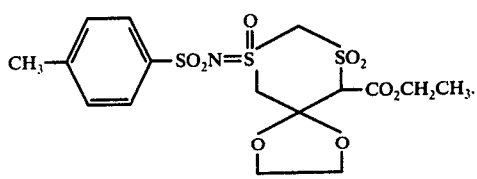
30. The compound
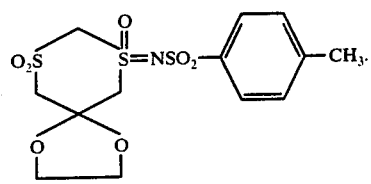
31. The compound
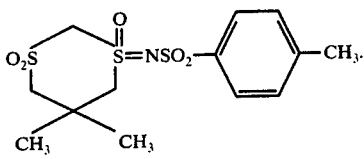
32. The compound
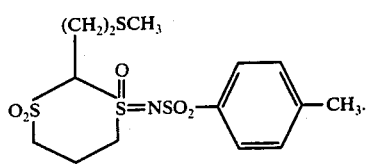
33. The compound
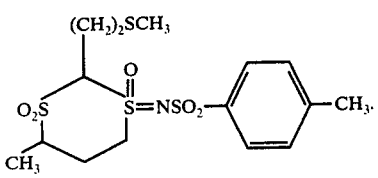
34. The compound
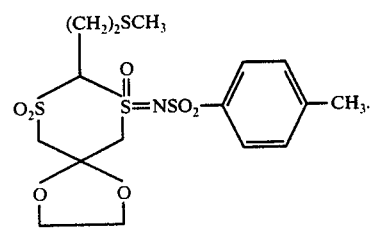
35. The compound
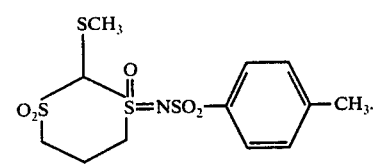
36. The compound
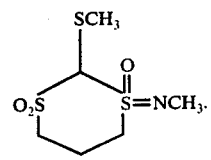
37. The compound
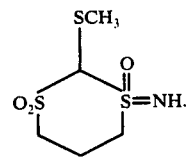
38. The compound
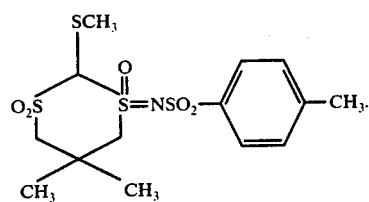
39. The compound
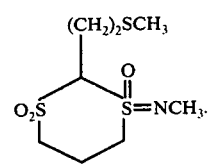
40. The compound
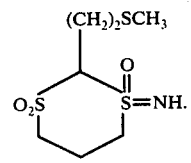
41. The compound
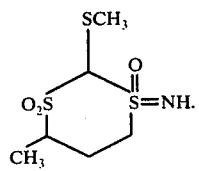
42. The compound
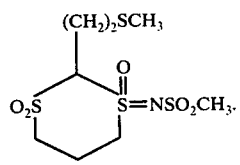
43. The compound

44. The compound

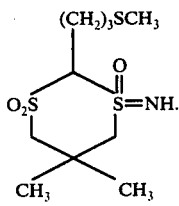

45. A compound of the formula

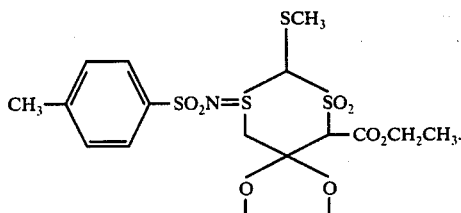

wherein $R^1$ is selected from hydrogen, alkyl containing 1 to 4 carbon atoms and —$CO_2R^4$ wherein $R^4$ is alkyl containing 1 to 4 carbon atoms; $R^2$ and $R^3$ when taken individually are selected from hydrogen and alkyl containing 1 to 4 carbon atoms and $R^2$ and $R^3$ when taken together are spiro.

46. A compound as defined in claim 45 wherein $R^1$ is hydrogen.

47. A compound as defined in claim 45 wherein $R^1$ is alkyl.

48. A compound as defined in claim 45 wherein $R^1$ is $CO_2R^4$.

49. A compound as defined in claim 45 wherein $R^2$ and $R^3$ are hydrogen.

50. A compound as defined in claim 45 wherein $R^2$ and $R^3$ are alkyl.

51. A compound as defined in claim 45 wherein $R^2$ and $R^3$ are spiro [1,3-dioxolane-2].

52. The compound

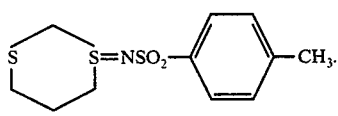

53. The compound

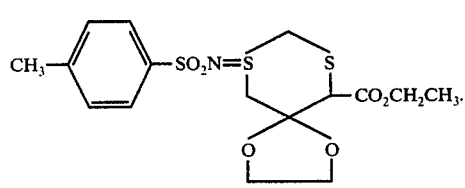

54. The compound

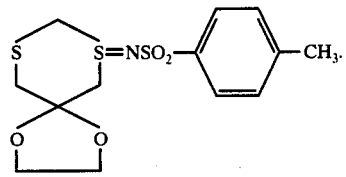

55. The compound

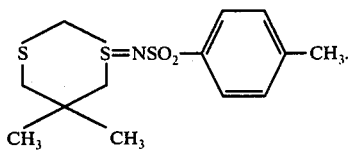

56. A method which comprises reacting (a) a 1,3-dithiane unsubstituted in the 2-position having the formula

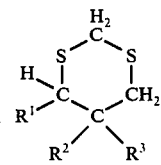

wherein $R^1$ is selected from hydrogen, alkyl containing 1 to 4 carbon atoms and —$CO_2R^4$ wherein $R^4$ is alkyl containing 1 to 4 carbon atoms; $R^2$ and $R^3$ when taken individually are selected from hydrogen and alkyl containing 1 to 4 carbon atoms and $R^2$ and $R^3$ when taken together are spiro and (b) N-chloro-p-toluenesulfonamide sodium salt in aqueous alkanol at a temperature between about 20° and 30° C to yield the corresponding 1-tosylimino-1,3-dithiane and isolating said 1-tosylimino-1,3-dithiane.

57. A method as defined in claim 56 wherein said (a) is

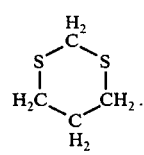

58. A method as defined in claim 56 wherein said (a) is

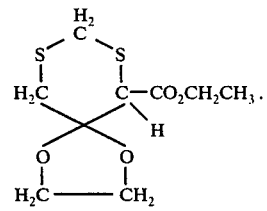

59. A method as defined in claim 56 which includes the additional step of reacting said 1-tosylimino-1,3-dithiane with peracetic acid in glacial acetic acid to yield the corresponding 1-tosylimino-1,3-dithiane-3,3-dioxide.

60. A method as defined in claim 59 which includes the additional step of reacting said 1-tosylimino-1,3-dithiane-3,3-dioxide with potassium permanganate in acetic acid-acetic anhydride solution at about 20° to 30° C to yield the corresponding 1-tosylimino-1,3-dithiane-1,3,3-trioxide.

61. A method as defined in claim 56 which includes the step of reacting said 1-tosylimino-1,3-dithiane with potassium permanganate in acetic acid-acetic anhydride solution at about 20° to 30° C to yield the corresponding 1-tosylimino-1,3-dithiane-1,3,3-trioxide.

62. The method of claim 61 which includes the additional step of reacting said 1-tosylimino-1,3-dithiane-1,3,3-trioxide with concentrated sulfuric acid at 25° to 90° C to yield the corresponding 1-imino-1,3-dithiane-1,3,3-trioxide.

63. A method as defined in claim 61 which includes the additional step of reacting said 1-tosylimino-1,3-dithiane-1,3,3-trioxide and at least one molar equivalent of an alkylating agent, $R^oS(CH_2)_nX$ wherein $n$ is 0, 2, 3, 4 or 5, $R^o$ is alkyl containing 1 to 4 carbon atoms and X is chloro or tosylate in the presence of an anion-forming base at a temperature not exceeding 100° C to yield the corresponding 1-tosylimino-2-$(CH_2)_nSR^o$-1,3-dithiane-1,3,3-trioxide.

64. A method as defined in claim 63 which includes the additional step of reacting said 1-tosylimino-2-$(CH_2)_nSR^o$-1,3-dithiane-1,3,3-trioxide with concentrated sulfuric acid at 25° to 90° C to yield the corresponding 1-imino-2-$(CH_2)_nSR^o$-1,3-dithiane-1,3,3-trioxide wherein $n$ and $R^o$ are as defined in claim 63.

65. A method as defined in claim 64 which includes the additional step of reacting said 1-imino-2-$(CH_2)_nSR^o$-1,3-dithiane-1,3,3-trioxide with an alkane sulfonyl chloride to yield the corresponding 1-alkylsulfonylimino-2-$(CH_2)_nSR^o$-1,3-dithiane-1,3,3-trioxide.

66. A method as defined in claim 64 which includes the additional step of reacting said 1-imino-2-$(CH_2)_nSR^o$-1,3-dithiane-1,3,3-trioxide with an alkylfluorosulfonate to yield the corresponding 1-alkylimino-2-$(CH_2)_nSR^o$-1,3-dithiane-1,3,3-trioxide.

67. A method as defined in claim 62 which includes the additional step of reacting said 1-imino-1,3-dithiane-1,3,3-trioxide with at least one molar equivalent of an alkylating agent $R^oS(CH_2)_nX$ wherein $n$ is 0, 2, 3, 4 or 5, $R^o$ is alkyl containing 1 to 4 carbon atoms and X is chloro or tosylate in the presence of an anion-forming base at a temperature not exceeding about 100° C to yield the corresponding 1-imino-2-$(CH_2)_nSR^o$-1,3-dithiane-1,3,3-trioxide.

68. A method as defined in claim 67 which includes the additional step of reacting said 1-imino-2-$(CH_2)_nSR^o$-1,3-dithiane-1,3,3-trioxide with an alkylfluorosulfonate to yield the corresponding 1-alkylimino-2-$(CH_2)_nSR^o$-1,3-dithiane-1,3,3-trioxide.

69. A method as defined in claim 67 which includes the additional step of reacting said 1-imino-2-$(CH_2)_nSR^o$-1,3-dithiane-1,3,3-trioxide with an alkane sulfonyl chloride to yield the corresponding 1-alkylsulfonylimino-2-$(CH_2)_nSR^o$-1,3-dithiane-1,3,3-trioxide.

70. A method as defined in claim 56 wherein said (a) is

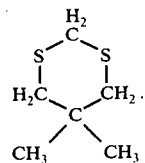

71. A method as defined in claim 56 wherein said (a) is

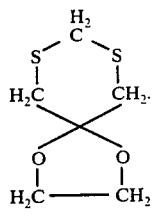

* * * * *